(12) United States Patent
Shurtliff et al.

(10) Patent No.: US 11,839,350 B2
(45) Date of Patent: Dec. 12, 2023

(54) ULTRASOUND TRANSDUCER SYSTEM FOR WEARABLE MONITORING DEVICE

(71) Applicant: Monovo, LLC, Orem, UT (US)

(72) Inventors: Jarom Shurtliff, Kaysville, UT (US); Adam Kaleo Roberts, Provo, UT (US); Jonathan Muñoz, West Jordan, UT (US); Christopher Hogstrom, Marion, IA (US); Steven Ray Taylor, Millcreek, UT (US); Paul Randal Cloward, Draper, UT (US)

(73) Assignee: MONOVO, LLC, Orem, UT (US)

( * ) Notice: Subject to any disclaimer, the term of this patent is extended or adjusted under 35 U.S.C. 154(b) by 0 days.

(21) Appl. No.: 17/052,477

(22) PCT Filed: May 3, 2019

(86) PCT No.: PCT/US2019/030653
§ 371 (c)(1),
(2) Date: Nov. 2, 2020

(87) PCT Pub. No.: WO2019/213559
PCT Pub. Date: Nov. 7, 2019

(65) Prior Publication Data
US 2021/0169443 A1    Jun. 10, 2021

Related U.S. Application Data

(60) Provisional application No. 62/666,579, filed on May 3, 2018, provisional application No. 62/666,567, filed
(Continued)

(51) Int. Cl.
A61B 5/08    (2006.01)
A61B 5/28    (2021.01)
(Continued)

(52) U.S. Cl.
CPC .......... *A61B 5/0816* (2013.01); *A61B 5/0022* (2013.01); *A61B 5/024* (2013.01);
(Continued)

(58) Field of Classification Search
CPC ..... A61B 5/0816; A61B 5/024; A61B 5/6823; A61B 5/6824; A61B 5/6831; A61B 8/02;
(Continued)

(56) References Cited

U.S. PATENT DOCUMENTS 7,559,894 B2    7/2009    McEowen
8,465,433 B2    6/2013    Zwirn
(Continued)

FOREIGN PATENT DOCUMENTS

EP    3494894 A1 *    6/2019
JP    2014-533974 A    12/2014
(Continued)

OTHER PUBLICATIONS

International Search Report and Written Opinion received for PCT Patent Application No. PCT/US2019/030653, dated Jul. 17, 2019, 7 pages.
(Continued)

*Primary Examiner* — Sean D Mattson
*Assistant Examiner* — Michael Yiming Fang
(74) *Attorney, Agent, or Firm* — Workman Nydegger

(57) ABSTRACT

Disclosed herein are systems, devices, and methods for providing continuous, non-invasive blood pressure monitoring. A wearable monitoring device includes first and second transducer arrays separated by a fixed distance. Each of the transducer arrays includes a plurality of independent transducer elements for transmitting and receiving ultrasound energy. When a user wears the device, the transducers are positioned near the brachial artery. The device operates to measure the transit time of a cardiac pulse through the
(Continued)

brachial artery and across the fixed distance between transducer arrays. The measured pulse transit time may then be used for determining pulse wave velocity and/or blood pressure.

23 Claims, 7 Drawing Sheets

Related U.S. Application Data on May 3, 2018, provisional application No. 62/666,576, filed on May 3, 2018.

(51) Int. Cl.

| | |
|---|---|
| *A61B 5/0205* | (2006.01) |
| *A61B 5/113* | (2006.01) |
| *A61B 5/00* | (2006.01) |
| *A61B 8/02* | (2006.01) |
| *A61B 8/00* | (2006.01) |
| *A61B 8/08* | (2006.01) |
| *A61B 5/024* | (2006.01) |
| *G06F 21/62* | (2013.01) |

(52) U.S. Cl.
CPC ............ *A61B 5/0205* (2013.01); *A61B 5/113* (2013.01); *A61B 5/28* (2021.01); *A61B 5/6823* (2013.01); *A61B 5/6824* (2013.01); *A61B 5/6831* (2013.01); *A61B 5/6832* (2013.01); *A61B 5/742* (2013.01); *A61B 5/7405* (2013.01); *A61B 8/02* (2013.01); *A61B 8/4281* (2013.01); *A61B 8/4494* (2013.01); *A61B 8/488* (2013.01); *A61B 8/5207* (2013.01); *A61B 8/565* (2013.01); *G06F 21/6254* (2013.01)

(58) Field of Classification Search
CPC ..... A61B 8/4281; A61B 8/4494; A61B 8/488; A61B 8/5207; A61B 8/565; A61B 8/00; A61B 8/04; A61B 8/06; A61B 5/0205; A61B 5/113; A61B 5/02125; A61B 8/4483; A61B 8/4272; A61B 8/4461; A61B 8/4477; A61B 8/44
See application file for complete search history.

(56) References Cited

U.S. PATENT DOCUMENTS

| | | | |
|---|---|---|---|
| 9,808,206 B1 | 11/2017 | Zhao et al. | |
| 2002/0055680 A1* | 5/2002 | Miele ...................... | A61B 8/04 600/450 |
| 2005/0171443 A1 | 8/2005 | Gorenberg et al. | |
| 2006/0287600 A1* | 12/2006 | McEowen ................ | A61B 8/12 600/481 |
| 2007/0167753 A1* | 7/2007 | Van Wyk ............. | A61B 8/4281 600/437 |
| 2009/0018409 A1 | 1/2009 | Banet et al. | |
| 2011/0066062 A1 | 3/2011 | Banet et al. | |
| 2011/0077526 A1* | 3/2011 | Zwirn .................... | A61B 8/145 600/459 |
| 2011/0209373 A1 | 9/2011 | Padgett et al. | |
| 2013/0131484 A1 | 5/2013 | Pernu et al. | |
| 2013/0172691 A1 | 7/2013 | Tran | |
| 2014/0228657 A1 | 8/2014 | Palley et al. | |
| 2014/0276123 A1 | 9/2014 | Yang | |
| 2015/0094544 A1 | 4/2015 | Spolin et al. | |
| 2015/0366535 A1* | 12/2015 | Eggers ................. | A61B 8/4245 382/131 |
| 2016/0206277 A1 | 7/2016 | Bidichandani et al. | |
| 2016/0302674 A1 | 10/2016 | Moyer et al. | |
| 2016/0354032 A1 | 12/2016 | Wariar | |
| 2017/0042504 A1* | 2/2017 | Rich .................... | A61B 8/0883 |
| 2017/0143309 A1 | 5/2017 | Seki et al. | |
| 2017/0156593 A1 | 6/2017 | Ferber et al. | |
| 2017/0231598 A1 | 8/2017 | Baek et al. | |
| 2017/0251967 A1 | 9/2017 | Premsukh | |
| 2018/0000447 A1* | 1/2018 | Stindel ................ | A61B 8/0875 |
| 2018/0078154 A1* | 3/2018 | Knickerbocker ...... | A61B 5/002 |
| 2018/0082051 A1 | 3/2018 | Johnson et al. | |
| 2018/0092622 A1* | 4/2018 | Duerr ...................... | A61B 8/42 |
| 2018/0303419 A1 | 10/2018 | Munoz et al. | |
| 2021/0169369 A1 | 6/2021 | Shurtliff et al. | |
| 2021/0244281 A1 | 8/2021 | Cloward et al. | |
| 2021/0282748 A1* | 9/2021 | Stehle .................. | A61B 8/4227 |

FOREIGN PATENT DOCUMENTS

| | | | | |
|---|---|---|---|---|
| WO | 2004/084720 A2 | 10/2004 | | |
| WO | WO-2013068955 A1 * | 5/2013 | ............ | A61B 5/022 |
| WO | 2015/074007 A1 | 5/2015 | | |
| WO | 2015/113054 A1 | 7/2015 | | |
| WO | 2016/205813 A1 | 12/2016 | | |

OTHER PUBLICATIONS

International Search Report and Written Opinion received for PCT Patent Application No. PCT/US2019/030670, dated Jul. 22, 2019, 9 pages.
International Search Report and Written Opinion received for PCT Patent Application No. PCT/US2019/030685, dated Jul. 12, 2019, 10 pages.
Extended European Search Report received for EP Patent Application No. 19795870.5, dated Dec. 1, 2021, 7 pages.
European search report dated Feb. 14, 2022 for EP Application No. 19797029.
European search report dated Feb. 23, 2022 for EP Application No. 19796520.
European Search Report received for EP Patent Application No. 19797029.6, dated May 16, 2022, 10 pages.
Office Action received for Japanese Patent Application No. 2021-510291, dated Apr. 6, 2023, 6 pages (3 pages of English Translation and 3 pages of Original Document).
Office Action received for Japanese Patent Application No. 2021-510291, dated Dec. 27, 2022, 8 pages (5 pages of English Translation and 3 pages of Original Document).
Freescale Semiconductor MPXM2051G Series Datasheet, Rev 2, Oct. 2009 (Year: 2009).

\* cited by examiner

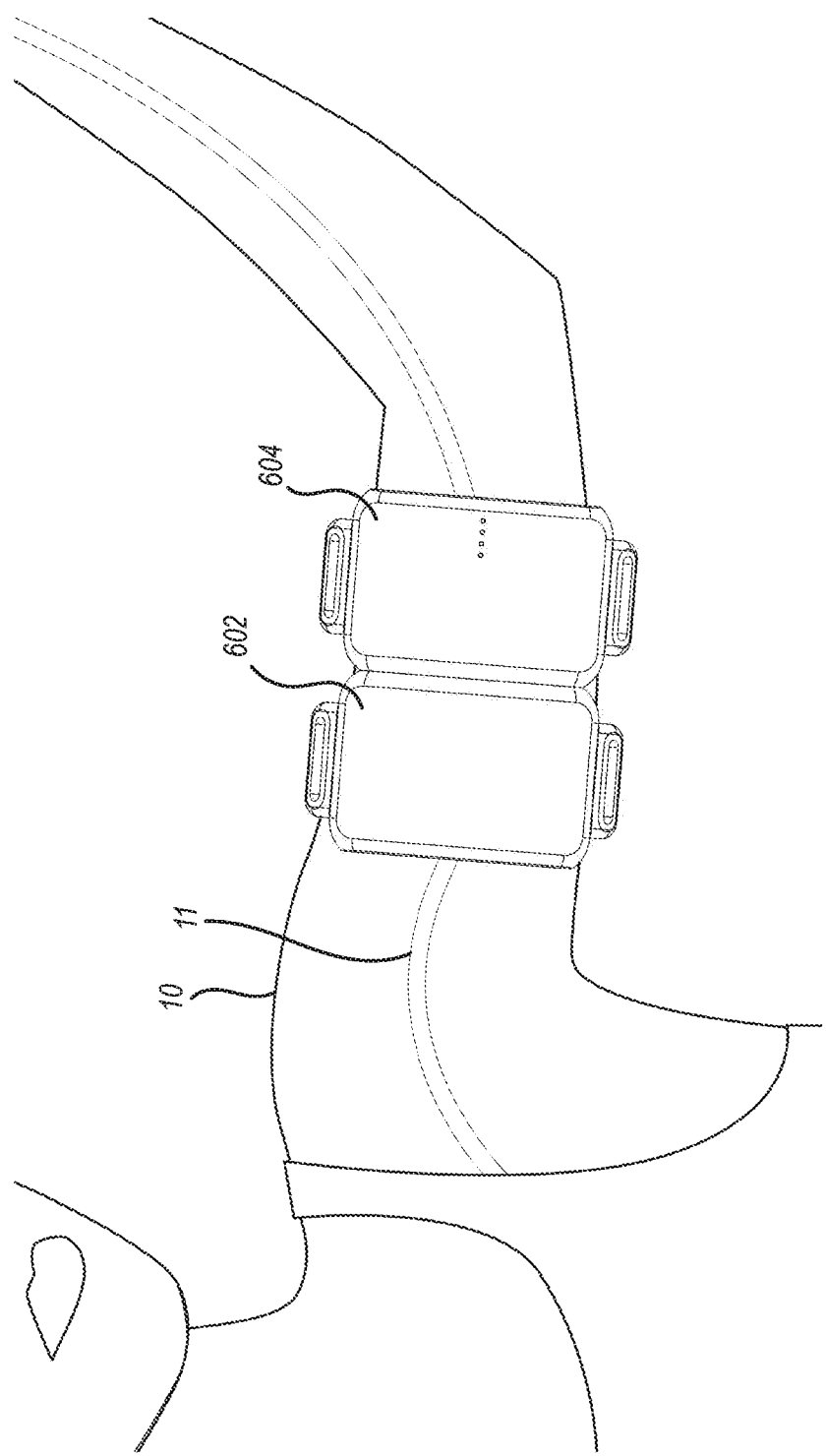

ULTRASOUND TRANSDUCER SYSTEM FOR WEARABLE MONITORING DEVICE

CROSS-REFERENCE TO RELATED APPLICATIONS

The present application is a 371 US Nationalization of PCT International Patent Application No. PCT/US2019/030653, filed May 3, 2019, which claims priority to US Provisional Patent Application No(s). 62/666,567, 62/666,576, and 62/666,579, all filed on May 3, 2018. The entire content of each of the foregoing patent applications is incorporated herein by reference.

BACKGROUND

Determining a patient's blood pressure is key to monitoring their health. There are many conventional techniques used to measure blood pressure. Among the common methods for measuring blood pressure are the auscultatory method and the oscillometric method. These methods are non-invasive and require the use of an inflatable cuff. Auscultation requires a clinician to perform the measurement, while oscillometry can be performed automatically by an electronic system. Although non-invasive, these methods are intermittent and therefore limited in how often they can provide blood pressure measurements. In addition, the inflatable cuff may be uncomfortable for some patients.

Another conventional method involves direct pressure measurement using a pressure sensor on the end of an artery catheter. This technique has the benefit of supplying continuous measurements. However, this technique also requires an invasive procedure to insert the catheter as well as careful effort from trained medical professionals to place and monitor the catheter. Thus, the current methods for measuring blood pressure suffer from intermittent monitoring (e.g., the auscultatory and osillometric methods) or invasive procedures (e.g., the pressure sensor artery catheter).

Accordingly, there is a long felt and ongoing need for blood pressure monitoring systems and methods capable of overcoming the limitations of the conventional techniques. In particular, there is need for improved systems and methods capable of non-invasively providing reliable blood pressure measurements in a continuous fashion.

SUMMARY

The present disclosure describes monitoring systems, wearable monitoring devices, and related methods for determining a pulse transit time (PTT) that can optionally be used to estimate blood pressure. Pulse transit time (PTT) is the time it takes for a blood pressure pulse from a heartbeat to arrive at two different sites in the arterial tree. The obtained PTT measurements may also be utilized to determine pulse wave velocity (PWV) and/or blood pressure.

In one embodiment, a wearable monitoring device includes a first transducer array and a second transducer array each attached to a wearable fixture and each structurally separated from one another by a fixed distance. The first and second transducer arrays include a plurality of independent transducer elements for transmitting and receiving ultrasound energy. The wearable monitoring device also includes an electronics assembly operatively coupled to the first and second transducer arrays. The electronics assembly includes one or more control components, such as a microprocessor and related memory device(s), for determining PTT across the fixed distance between the first and second transducer arrays.

In some embodiments, the wearable monitoring device includes a wearable fixture, which may include one or more bands for securing the device to a user at a suitable location where arterial blood flow may be measured. In a preferred implementation, the monitoring device is configured to be worn on the user's upper arm, with the first and second transducer arrays oriented to be on the inner arm near the brachial artery.

In some embodiments, one or both of the transducer arrays include about 5 to 30, or about 8 to 25, or about 12 to 20 independent transducer elements. The use of multiple independent transducer elements within an array beneficially increases the quality of the reading. That is, the odds are increased that at least one of the transducer elements will be properly positioned relative to the user's artery to pass an effective ultrasound signal and/or to receive an effective reflected Doppler signal. Thus, only one transducer element in each array is needed at a time.

Other more conventional arrays may alternatively be utilized, such as those that use beamforming. However, the illustrated transducer arrays, configured to utilize a single transducer element in each array at a time, are preferred as a simple, robust, and cost-effective design.

A transducer array may have a length of about 0.5 to 4 inches, or about 1 to 2.5 inches. When the device is worn, the transducer arrays are oriented transverse (e.g., substantially orthogonal) to the brachial artery, increasing the likelihood that at least one ultrasound beam emanating from an array element will intersect a portion of the artery. Alternatively, other arrays used in conventional ultrasound imaging could be used using phased array beamforming and associated ultrasound signal processing.

The preferred method is to use dedicated array element pairs (transmitter and receiver) as described, since the arrays and processing electronics are simpler and more robust. Finally, an array (e.g., consisting of as little as one but preferably at least three elements) could be positioned in the transverse direction and configured to be moveable by a stepper motor, gear, and/or other linear motion mechanism to effectively position the array in the proper location nearest the artery. Signal strengths from adjoining elements could be used to determine the direction to move the array so that a portion of the artery will intersect each array.

In some embodiments, the microprocessor or other suitable control element operates to select a particular subset of transmitter elements within the transducer array through which ultrasound energy is transmitted and/or select a particular subset of receiver elements within the transducer array through which a reflected ultrasound signal is obtained. This contrasts with many contemporary medical ultrasound systems, which commonly select all transducers elements at the same time to function as an electronically steered or phased array (ESA) to focus ultrasound energy. Such a method requires relatively complex 3D ultrasound signal processing.

Additional features and advantages will be set forth in part in the description that follows. It is to be understood that both the foregoing summary and the following detailed description are exemplary and explanatory only, and are not to be read as limiting the disclosure to any particular set of embodiments.

BRIEF DESCRIPTION OF THE DRAWINGS

A more particular description will be rendered by the embodiments illustrated in the appended drawings. It is appreciated that these drawings depict only exemplary embodiments of the disclosure and are therefore not to be considered limiting of its scope. In the accompanying drawings:

FIG. 2C illustrates an implementation of the monitoring device of FIGS. 2A and 2B by placement on a user's upper arm to direct ultrasound to the brachial artery;

DETAILED DESCRIPTION

Figure 1A:
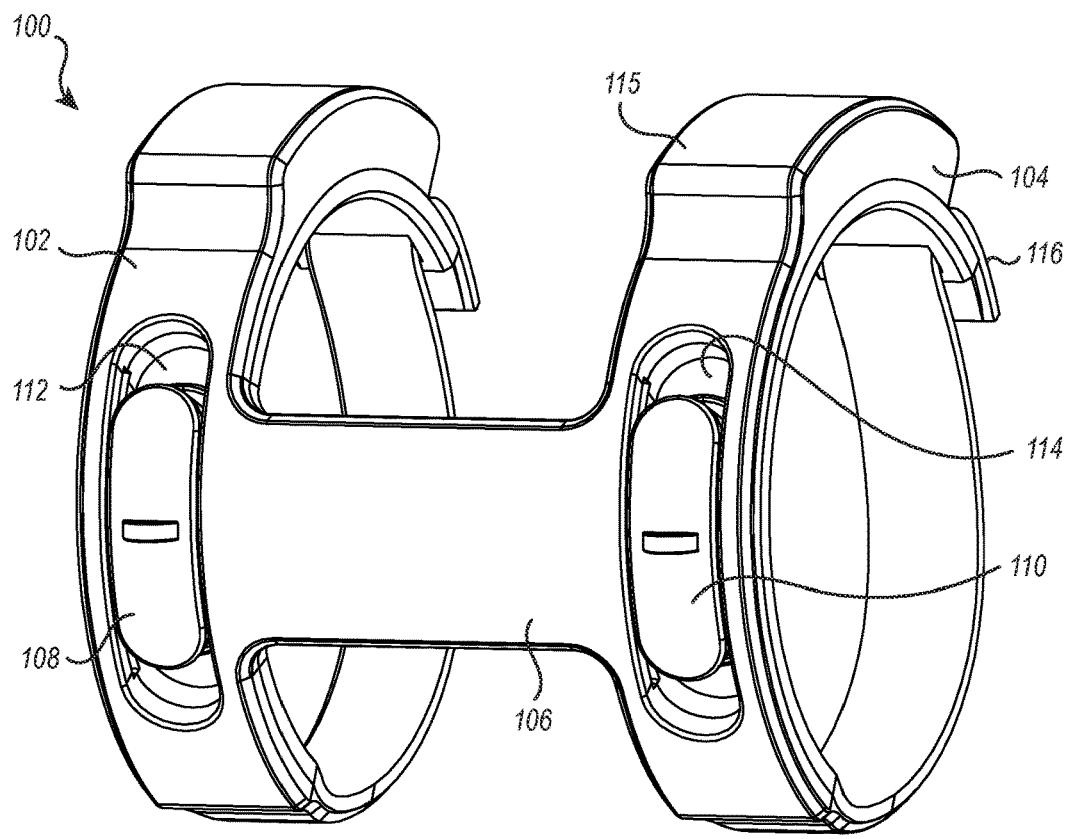
FIG. 1A illustrates an exemplary monitoring device including a proximal sensor assembly and a distal sensor assembly.

FIG. 1A illustrates an exemplary wearable monitoring device 100 configured to enable continuous and non-invasive monitoring of a user's blood pressure. The monitoring device 100 functions by measuring the pulse transit time (PTT) through an artery that the device is brought into proximity to. In a typical embodiment, the monitoring device 100 is configured to be worn on the user's upper arm, making use of the brachial artery for measuring PTT. However, the features described herein may also be utilized in embodiments sized for placement at other anatomical locations, such as at a leg or wrist.

The wearable monitoring device 100 utilizes two separate ultrasound transducer arrays (one proximal and one distal), each respectively housed in housings 108 and 110. The arrays operate to perform continuous wave Doppler ultrasound on the brachial artery. Although continuous wave Doppler is preferred, some implementations may utilize other modalities such as pulsed wave Doppler. The ultrasound arrays measure the velocity (e.g., to within a scale factor) of the blood flowing through the brachial artery.

The monitoring device 100 measures PTT by using ultrasound to monitor the time delay between a blood flow pulse at the proximal array and the same flow pulse at the distal array. In operation, signals at each of the two locations are measured to determine the time difference between the same cardiac event. The cardiac event could be, for example, the beginning of systole, the peak systolic velocity, and/or the end systolic velocity. Thus, for a given cardiac event, the time between when the first ultrasound array (i.e., the proximal array) measures the signal and when the second ultrasound array (i.e., the distal array) measures the signal represents the PTT between each array.

The structure of the monitoring device 100 ensures that the separate transducer arrays are maintained a fixed distance apart from one another. This allows for a simple and straightforward calculation of pulse wave velocity (PWV) given the calculated PTT and the fixed distance between the ultrasound arrays. PWV strongly correlates to blood pressure. For example, a user's measured PWV can be correlated to blood pressure by obtaining a suitable number of direct blood pressure measurements (e.g., through the conventional auscultatory method) and determining a calibration curve when the monitoring device is used on a patient for the first time.

The illustrated monitoring device 100 includes a wearable fixture having a first band 102 and a second band 104. When worn by the user, one band will be located proximally and the other will be located distally with respect to arterial blood flow. Each band 102, 104 also includes a coupler 116 allowing the bands to be custom sized to fit an individual user. The couplers 116 may be formed as buckles, clasps, loops, or other suitable fastening means known in the art. The end portions of each band 102, 104 may include corresponding sections of hook and loop fastener material. The illustrated embodiment shows two separate bands 102 and 104.

Other embodiments may include a different number of bands and/or may replace one or more bands with a clasp or other fastening structure. For example, while at least two bands or equivalent fastening structures are preferred, one embodiment could employ a single band for securing to the user while relying on other longitudinal structures (e.g., longitudinal section 106) to maintain a fixed distance between housings 108, 110 and the transducer arrays contained therein.

The included longitudinal section 106 separates the first band 102 from the second band 104 and functions to structurally maintain separation between the separate measuring points of each band. For example, the longitudinal section 106 may be sized to separate the first housing 108 and the second housing 110 (and thus the arterial velocity measuring points) by about 1.5 to 6 inches, or more preferably about 2 to 4 inches. This range of separation beneficially balances the need to have sufficient distance to obtain accurate PTT results with the need to keep the overall length of the device 100 small enough for practical and comfortable use. Although devices with longer distances between measuring points may increase accuracy somewhat, the tradeoff in decreased wearability and comfort of the device has not been found to be worth the additional length.

The illustrated longitudinal section 106 is shown as a single piece of material extending between the receptacles 112 and 114 on the inner side of the device 100. Other embodiments may additionally or alternatively include other structural features for fixing the distance between the measurement points. For example, other embodiments may include one or more longitudinal sections that extend along an outer side, upper side, lower side, and/or other areas of the device 100.

Yet other embodiments may include a longitudinal section that fully wraps around or substantially wraps around the circumference of the user's arm. More preferred embodiments, however, minimize bulk and increase open space for breathability and comfort by limiting the width and circumferential coverage of the longitudinal section 106. For example, the circumference of the device 100 at a location between the bands 102 and 104 is preferably about 50% to about 90% open when the device is sized for and/or worn by a typical adult.

Each band 102 and 104 also respectively includes a receptacle 112 and 114. The receptacles 112 and 114 are sized to allow the housings 108 and 110 to slide within and be adjustable relative to the receptacles 112 and 114. This beneficially allows for more fine-tuned positioning of the housings 108 and 110 when the device 100 is being worn. One or more compartments 115 may also be built into the device 100 to house circuit boards, batteries, additional sensors, and/or other components as described in more detail below.

Figure 1B:
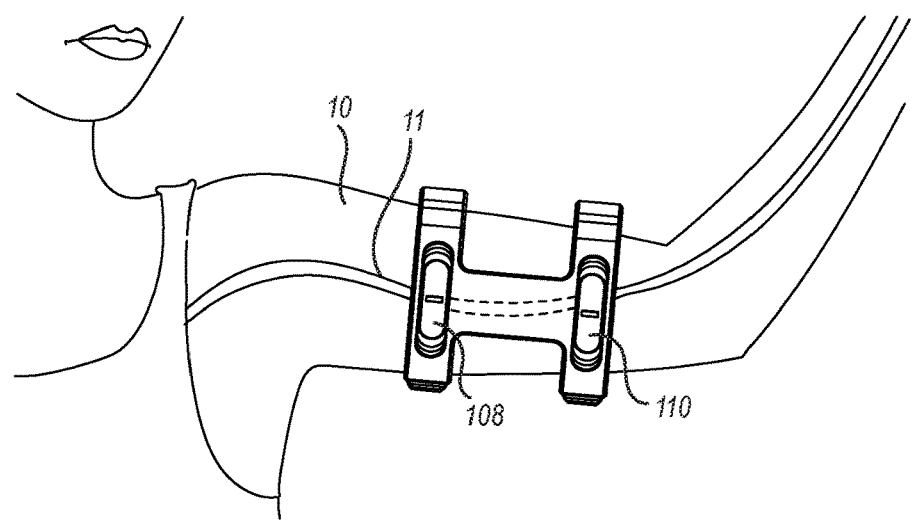
FIG. 1B illustrates one implementation of the monitoring device of FIG. 1A by placement on a user's upper arm to direct ultrasound to the brachial artery.

FIG. 1B schematically illustrates placement of the device 100 on a user's arm 10. The housings 108 and 110 are positioned on the inner side of the arm 10 to be adjacent the brachial artery 11. Because the brachial artery 11 typically isn't straight and may vary from user to user, the housings 108 and 110 may be transversely adjusted to a position that improves the signal. Although individual users may vary in anatomy and/or in the particular way they wear the device, the adjustability of the housings 108 and 110 increases the odds that a suitable signal will be obtainable in a wide variety of applications. In addition to the adjustability of the housings 108 and 110, the versatility of the device is increased by using ultrasound transducer arrays, which will be described in further detail below.

Figure 2A:
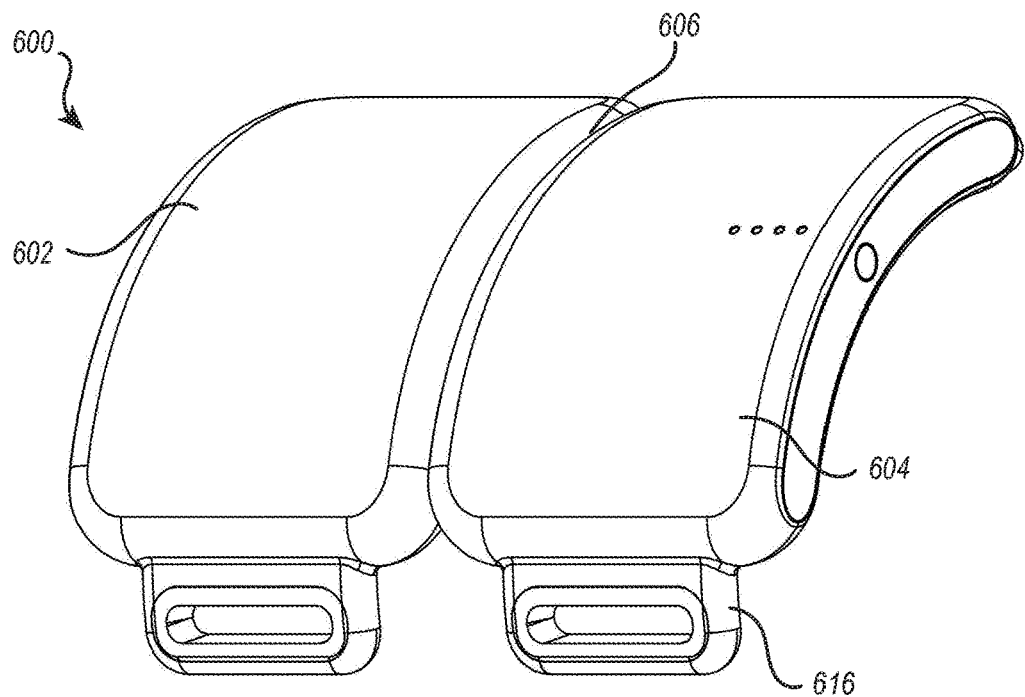
FIGS. 2A and 2B illustrate another embodiment of a monitoring device including both a proximal sensor assembly and a distal sensor assembly.
Figure 2B:
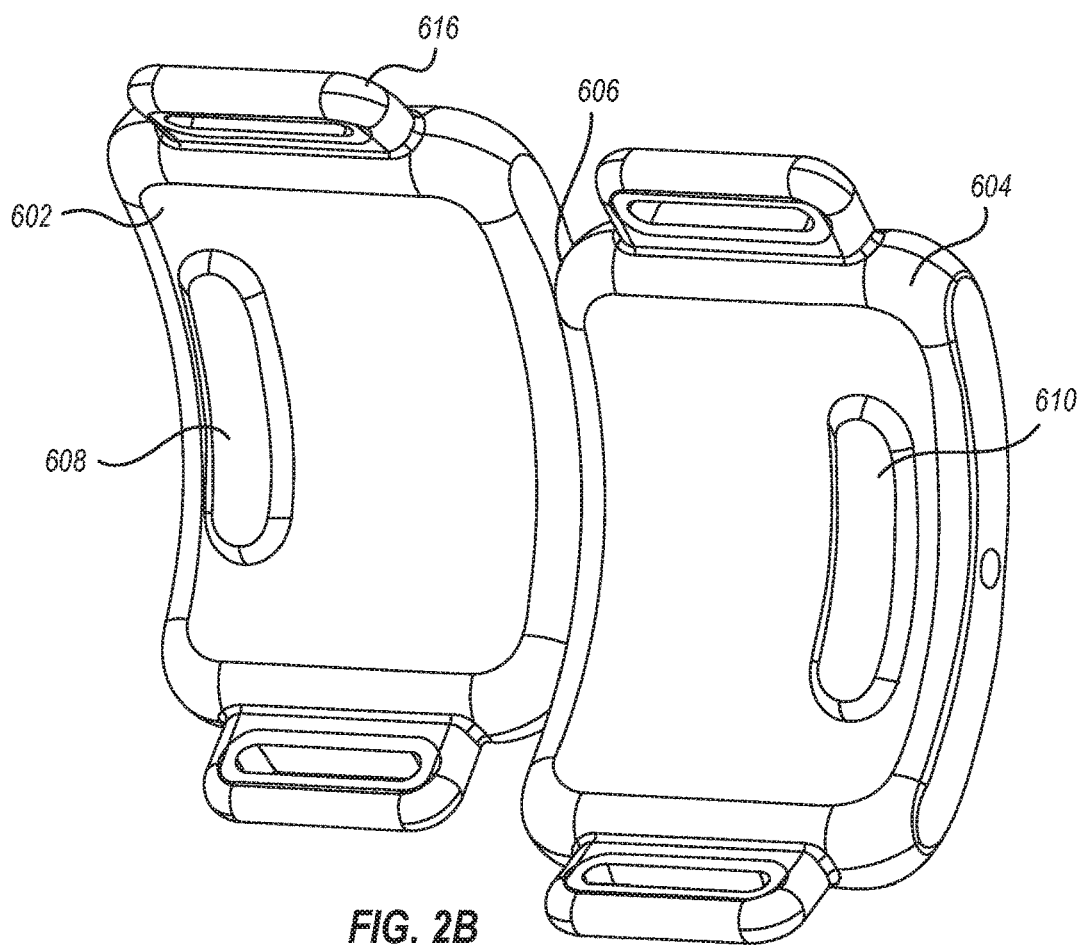

FIGS. 2A and 2B illustrate an alternative embodiment of a wearable monitoring device 600 that shares many structural and functional features with the wearable monitoring device 100. FIG. 2A shows an isometric view of the outer side of the device 600 while FIG. 2B shows an isometric view of the inner side of the device 600.

As with the device 100, the illustrated device 600 includes a first band 602, a second band 604, and a set of couplers 616. The couplers 616 are shown here as strap attachments, but may be additionally or alternatively configured as any of the other coupling means described herein.

Rather than using a distinct longitudinal section to separate the separate bands 602 and 604, the bands 602 and 604 are sized such that even when connected together along connection 606, the array housings 608 and 610 are maintained an adequate distance from one another. As with device 100, the distance between array housings may be about 1.5 to 6 inches, or more preferably about 2 to 4 inches to effectively balance measurement accuracy with wearability and comfort.

As shown best in FIG. 2B, the array housings 608 and 610 may be adjusted relative to one another by sliding the bands 602 and 604 relative to one another along slidable connection 606. As with device 100, such adjustability allows for effective device positioning for effective measurement. As shown, the bands 602 and 604 each have a curved profile that a conforming fit to the patient's arm and thereby allows the array housings 608 and 610 (which follow the same curved profile) to effectively interface against the patient's skin.

FIG. 2C illustrates placement of the device 600 on a user's arm 10. Array housings 608 and 610 are positioned on the inner side of the arm 10 to be adjacent the brachial artery 11. Because the brachial artery 11 typically isn't straight and may vary from user to user, the bands 602 and 604 may be slidably adjusted along slidable connection 606 to a position that improves the signal. Although individual users may vary in anatomy and/or in the particular way they wear the device, the adjustability of the bands 602 and 604 increases the odds that a suitable signal will be obtainable in a wide variety of applications.

Figure 3:
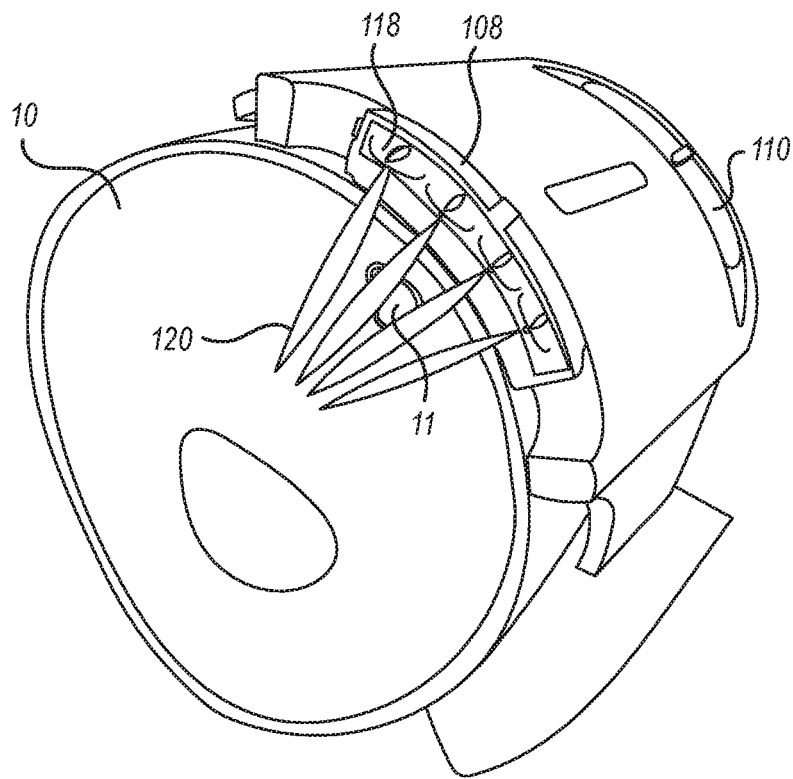
FIG. 3 illustrates a cross-sectional view of a user's arm and the monitoring device, showing an ultrasound transducer array directing ultrasound energy toward the brachial artery.

FIG. 3 illustrates a cross-sectional view of the monitoring device and the user's arm 10. In this view, the first transducer array 118 is visible within housing 108. As shown, the array 118 includes a plurality of ultrasound transducers (i.e., transducer elements) spanning a portion of the circumference of the device. Although not shown, it will be understood that a similar ultrasound transducer array is present within housing 110.

The use of multiple ultrasound transducers within the array 118 beneficially increases the odds of obtaining a good reading. Compared to a transducer arrangement with fewer transducers, the odds are greater that the ultrasound beam 120 of at least one transducer within the array 118 will intersect with the brachial artery 11 and at least one transducer will be positioned to effectively receive the return signal. The transducer array 118 preferably has a transverse/circumferential length that spans about 5% to about 25% of the circumference of the device when worn by a typical adult. This beneficially provides effective coverage of the cross-section of the patient's arm 10 without delivering excessive and needless coverage unlikely to reach the brachial artery 11 and potentially more likely to generate signal noise. The transducer array 118 may be, for example, about 0.5 inches to about 4 inches long, or more preferably about 1 to 2.5 inches long, such as about 1.5 inches long.

The ultrasound array 118 is focused at the general depth of the brachial artery 11. The penetration depth of ultrasound waves should be sufficient to detect the Doppler shift caused by the moving blood in the brachial artery 11 but should be limited to avoid getting unwanted signals. In a typical application, the targeted penetration depth is about 1 to 1.6 inches, or more preferably about 0.2 to 1.0 inches, though the ideal penetration depth for a particular patient may vary. The ultrasound frequency is also a factor in determining penetration depth. The frequency may be between about 1.5 MHz to about 7 MHz, or more preferably about 2 MHz to about 5 MHz. In a typical application, ultrasound frequencies within these ranges effectively balance the need for sufficient penetration depth to obtain a signal with the desire to limit excessive penetration and signal noise.

Figure 4A:
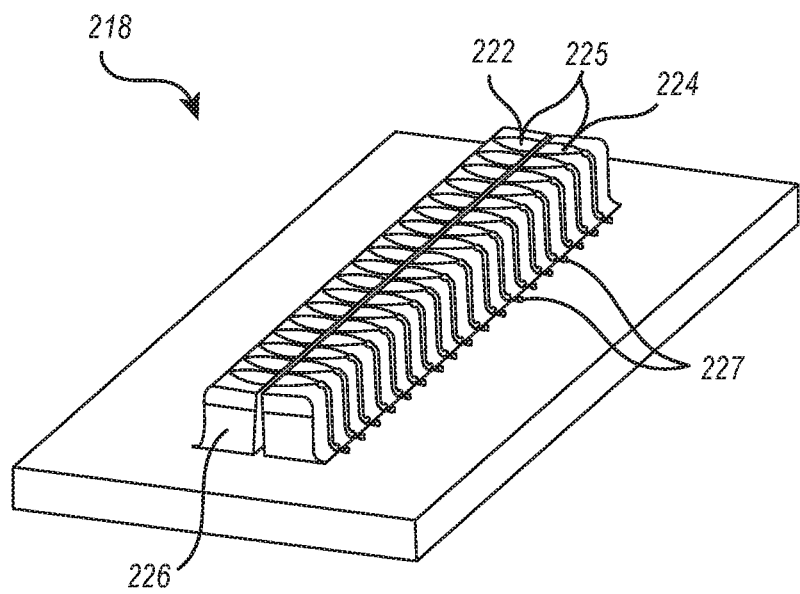
FIGS. 4A through 4D illustrate an exemplary ultrasound transducer array, showing various components and layers that may be utilized to form the array.

FIGS. 4A through 4D show successive layers in the construction of an exemplary transducer array 218. The transducer array 218 may be used as the transducer arrays in any of the embodiments described above. As shown in FIG. 4A, the array 218 includes a plurality of transmitter sections 222 aligned on one side of the array 218 and a plurality of receiver sections 224 aligned on the opposite side of the array 218. Each opposing transmitter and receiver form a separate transducer element 225. The transducer elements 225 are formed from copper and/or other suitable electrically conductive material and include lead lines 227 for coupling to other components of the device.

The shape of the conductive material defines the area of the piezo material that will be active during transmission or reception of the signal. As depicted herein it is in the shape of a half ellipse. This shape achieves a more uniform ultrasonic energy beam pattern radially about the beam axis as compared to similarly sized rectangular elements. The shape also achieves a tighter beam pattern in the elevation dimension (between Doppler transmitter/receiver pair elements) and a broader beam pattern in the azimuthal dimension (between elements in either the transmit or receive array). The elliptically surfaced elements beneficially achieve better Doppler point resolution along the artery, while maintaining good sensitivity (e.g., greater than about −6 dB) when switching between Doppler pair elements in the arrays. Elliptical-shaped elements are thus preferred, though circular, rectangular, or otherwise shaped elements may also be used in other embodiments.

The use of multiple independently functioning transducer elements provides greater versatility and increases the quality of the Doppler shift measurement. This is because for a given reading, the transducer with the strongest signal may be selected. This may change from measurement to measurement, from one period of use to the next (e.g., if the user removes the device and later reattaches it in a slightly different position), and/or from user to user (e.g., due to anatomical differences or wearing preferences). The capability of selecting from among multiple transducer elements allows for effective operation of the device in a variety of circumstances. The inclusion of about 5 to about 30 transducer elements, or more preferably about 8 to 25 transducer elements, or even more preferably about 12 to 20 transducer elements, provides these benefits without giving excessive measurement granularity and without requiring excessive bulk and/or expense to the device. The illustrated embodiment includes 18 independently functioning transducer elements 225.

The aligned transmitter sections 222 may be separated from the aligned receiver sections 224 by an isolation region 226. The isolation region 226 functions to electrically and acoustically separate each transmitter section 222 from its opposing receiver section 224 to minimize or prevent electric signals and ultrasound waves from propagating directly to the receiver section 224 from the transmitter section 222.

The transducer elements 225 are positioned on a block 226. The block 226 functions to orient the transducer elements 225 in a beneficial position for achieving effective focusing of the ultrasound signal. As shown, the block 226 is tilted/angled so that the upper surface (i.e., the innermost surface closest to the user's arm when the device is worn) has an angled, concave shape. The block 226 is preferably formed from material(s) with an acoustic impedance similar to that of air. This helps to prevent generated ultrasound waves from propagating through the block 226 and instead allows the waves to propagate away from the block toward the user.

Figure 4B:
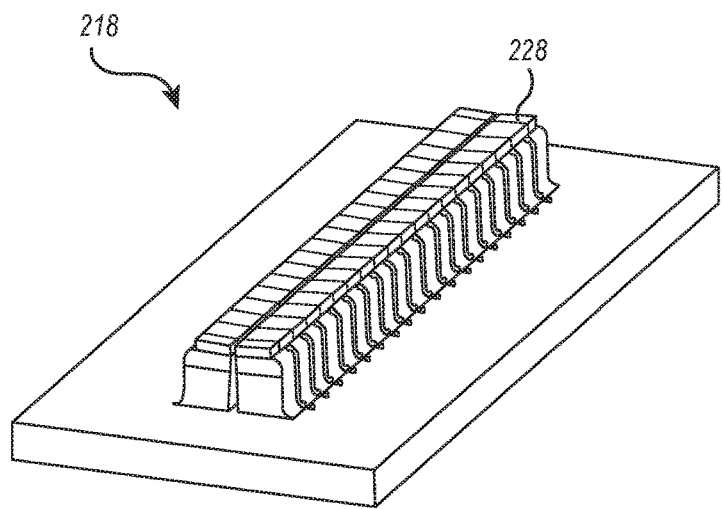

FIG. 4B illustrates placement of a piezoelectric material 228 upon the transducer elements 225, with part of the piezoelectric material 228 placed over the transmitter sections 222 and another separate part placed over the receiver sections 224. The piezoelectric material 228 on the transmitter side changes size and shape in response to voltages to thereby generate ultrasound waves. The piezoelectric material 228 on the receiver side receives reflected ultrasound waves and converts them to electric signals.

Figure 4C:
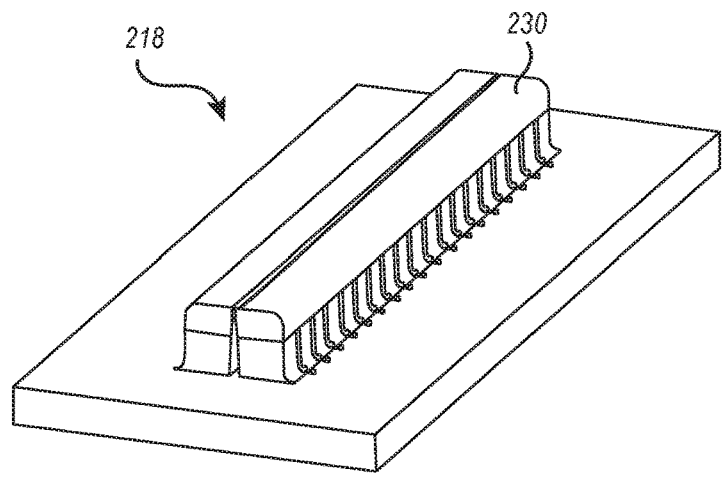

FIG. 4C illustrates placement of ground electrodes 230 to provide the second electrical connection to the piezoelectric material 228 and complete the circuit. The ground electrodes are formed of copper and/or other suitable conductive material. These shielding and ground electrodes may be covered with insulating materials except where electrical contact is needed. As shown, they may be added to substantially cover the piezoelectric material 228 and thereby provide electromagnetic shielding.

Figure 4D:
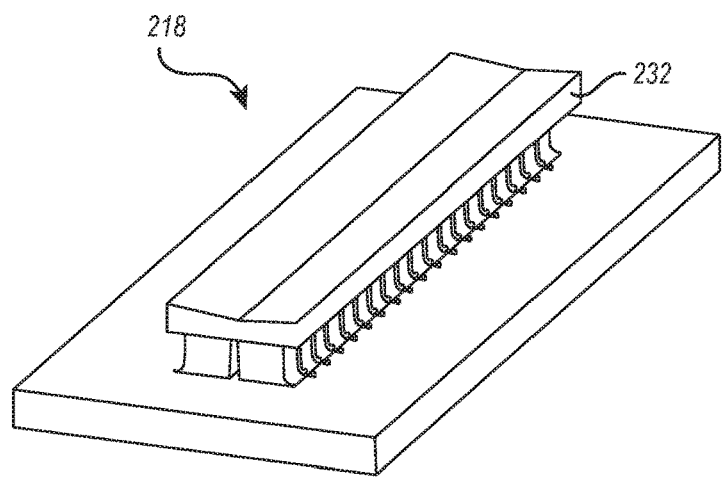

FIG. 4D illustrates placement of an acoustically-transparent material 232 on the array 218. The acoustically-transparent material 232 functions to provide electrical insulation between the user's arm and the ultrasound array's electrodes while still allowing ultrasonic waves to pass from the array 218 into the arm and to reflect from the arm back toward the array 218. This material can also be used to set the angle of the array in relationship to the flow of blood in the vessel. This is the so called doppler angle. The preferred angle where the doppler signal is greatest is 0 degrees. That would require the transducer to be placed inside and along the axis of the vessel, which is not feasible. An angle of about 30 degrees is achievable and has been found to produce good results. The acoustically-transparent material 232 may also slightly attenuate ultrasonic waves to prevent the waves from reverberating within the material. The acoustically-transparent material 232 may include a gel pad that acoustically couples the array 218 to the user's skin when the user wears the device. The gel pad may include, for example, propylene glycol, glycerine, carbomer, agarose, gelatin, other suitable gelling agents, or combinations thereof.

Figure 5:
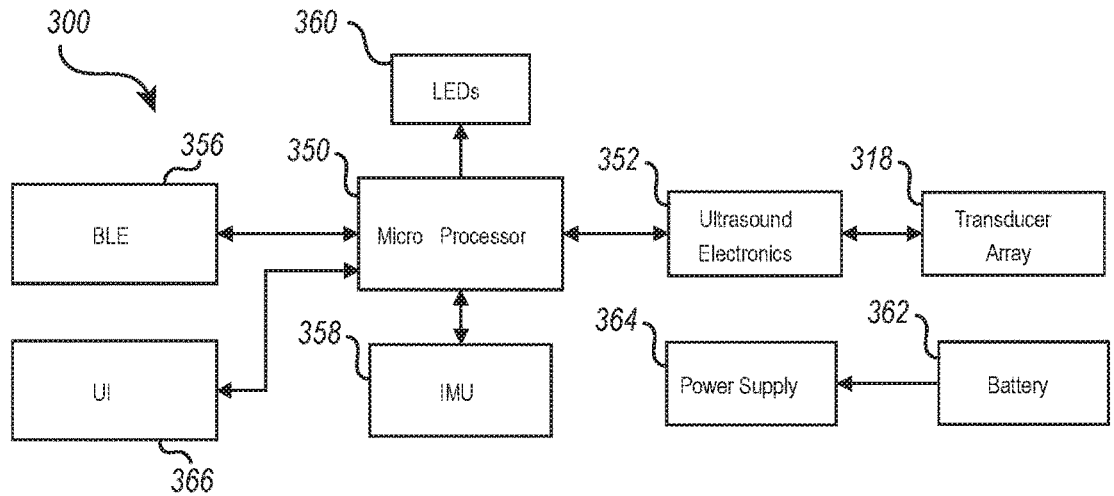
FIG. 5 schematically illustrates an electronics assembly that may be located within the monitoring device.

FIG. 5 schematically illustrates an electronics assembly 300 that may be located within the monitoring device 100, such as within compartment 115. An ultrasound electronics module 352 is communicatively coupled to each transducer array 318 (shown and referred to here as a single array 318 for simplicity). The ultrasound electronics assembly 352 is configured to drive the transducer array 318. For example, the ultrasound electronics module 352 may be configured to provide an excitation voltage to the transmitter sections of the transducer array 318 and to receive and digitize the return signals generated by the receiver sections of the transducer array 318.

The electronics assembly 300 also includes a microprocessor 350 (i.e., controller, logic device, etc.) communicatively coupled to the ultrasound electronics assembly 352. The microprocessor 350 is configured to provide logical control over the ultrasound electronics assembly 352 and to receive measured signals from the ultrasound electronics assembly 352. For example, the microprocessor 350 may be configured to execute specific operations to measure PTT based on the measured signals obtained from the transducer array 318.

The electronics assembly 300 also includes a communications module 356 communicatively coupled to the microprocessor 350. The communications module 356 is shown in this embodiment as a Bluetooth Low Energy (BLE) module, but other communication functionalities and network types may additionally or alternatively be utilized, such as the Internet, cellular RF networks, a local area network (LAN), a wide area network (WAN), and the like. The communications module 356 enables the electronics assembly to communicate data, including measured PTT readings, to an external computer system such as a smart phone, tablet, personal computer, and/or computer system associated with a healthcare facility or provider.

The electronics assembly 300 may also include a display assembly 360, shown here as a series of light-emitting diodes (LEDs). The display assembly 360 is communicatively coupled to the microprocessor 350 and is configured to provide information to the user via audio and/or visual effects. For example, the display assembly 360 may include, in addition to or as an alternative to LEDs, one or more of: a speaker, an information display screen, a status icon, or other display features. These display features may be configured to indicate one or more of device power or operational status, battery level, device operation mode, communication/pairing status, error state (or lack thereof), a warning message related to detected vital sign(s), or other device states of benefit to the user. A user interface 366 may also be included with input controls (e.g., buttons, dials, switches, etc.) allowing the user to interface with the device.

The electronics assembly 300 also includes a battery 362 and associated power supply 364 for powering the microprocessor 350, ultrasound electronics module 352, communications module 356, motion sensor 358, display module 360, and/or other components that may be included within the electronics assembly 300. The motion sensor 358 may include an inertial measurement unit (IMU) for measuring one or more motion and/or position states of the monitoring device. In one embodiment, the motion sensor 358 is a 9-axis sensor including a 3-axis gyroscope, a 3-axis accelerometer, and a 3-axis magnetometer (sometimes referred to as a 3-axis compass). Other embodiments may utilize other motion sensors, such as a 6-axis sensor including a 3-axis gyroscope and a 3-axis accelerometer.

Motion/position data detected using the motion sensor 358 may be utilized in conjunction with readings obtained using the transducer arrays 318 to obtain improved and/or calibrated vital sign measurements. For example, PTT readings derived from ultrasound measurements may be utilized to calculate and monitor the user's blood pressure. These readings, however, may at least partially depend on the position of the user's arm during measurement, particularly the height of the arm relative to the heart.

Motion/position data detected using the motion sensor 358 can beneficially improve the accuracy of such readings by enabling calibration based on a determined position of the monitoring device. In one embodiment, for example, a separate, secondary monitoring device having a similar motion sensor may be positioned at a relatively fixed location on the user (e.g., the user's torso) to enable detection of the position of the primary, arm-worn monitoring device relative to the separate monitoring device.

Figure 6:
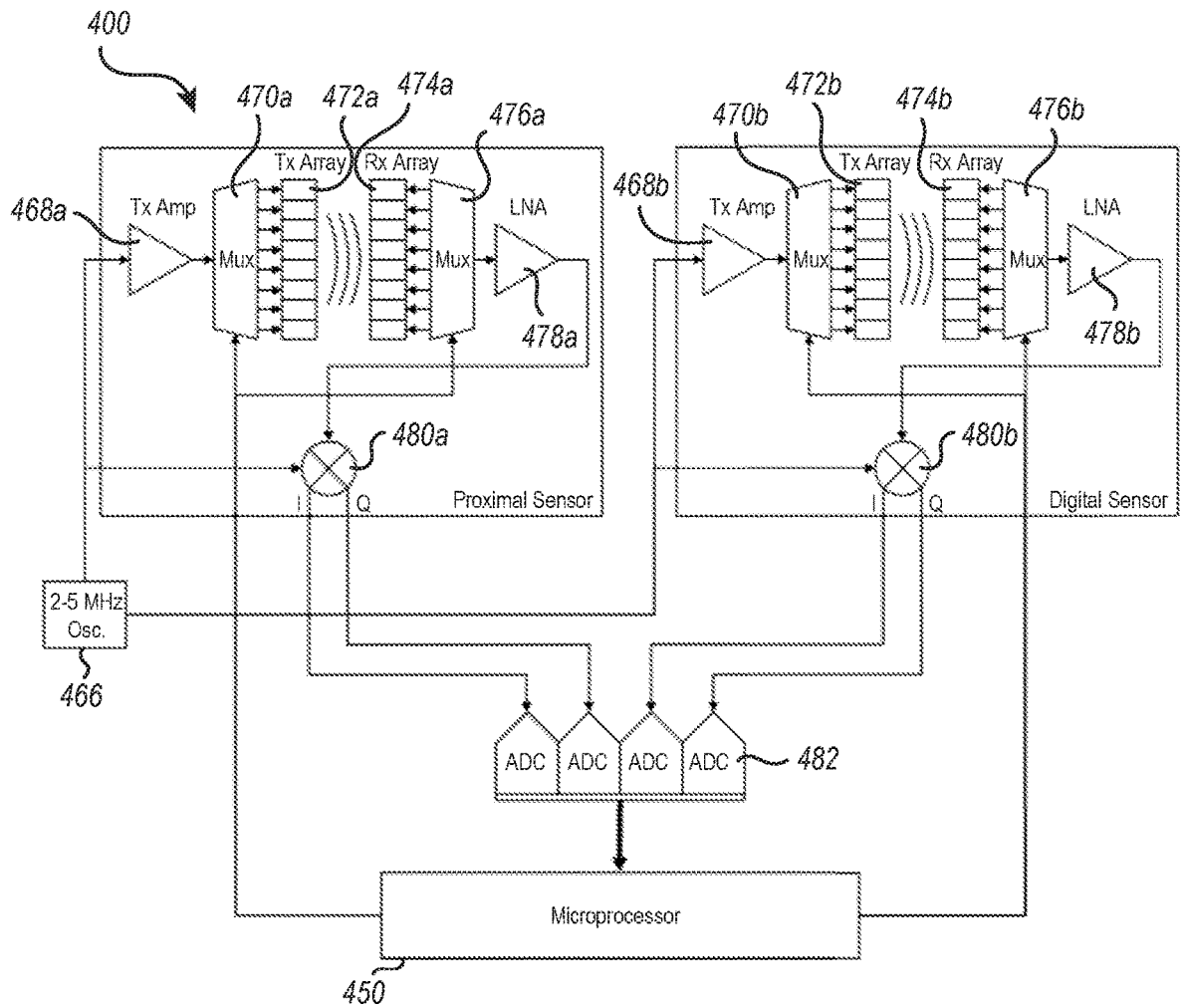
FIG. 6 schematically illustrates an exemplary system for operating ultrasound electronics and proximal and distal transducer arrays of the electronics assembly.

FIG. 6 schematically illustrates an exemplary system 400 for operating the ultrasound electronics and the proximal and distal transducer arrays. The system 400 may be utilized in any of the embodiments described above. In this embodiment, each of the proximal and distal sensors are similarly configured, with components of the proximal sensor having the subscript "a" and like components of the distal sensor having the subscript "b" for the same numerical label. For simplicity, the following discussion will typically refer collectively to each proximal and distal component in the singular without use of the subscripts, though it will be understood that the description applies to each of the proximal sensor and distal sensor components.

As shown, an oscillator 466 provides a signal for driving the generation of ultrasound waves at the transmitter array 472. The oscillator 466 may generate a sinusoidal signal with a frequency of about 2 MHz to about 5 MHz, for example. A transmission amplifier 468 may be used to amplify the generated signal before passing the signal to a transmission multiplexer 470. The transmitter array 472 and the corresponding receiver array 474 together form a transducer array, such as in the embodiment illustrated in FIGS. 4A through 4D.

The microprocessor 450 is controllably linked to the transmission multiplexer 470 and operates to determine which particular subset of transmitter element(s) within the transmitter array 470 will be used to transmit the ultrasound wave into the user's tissue. The microprocessor 450 is also controllably linked to the receiving multiplexer 476 and operates to determine which particular subset of receiving element(s) within the receiver array 474 will be used to obtain the reflected Doppler signal. This determination may be made in a number of ways. For example, the microprocessor 450 may initially and/or periodically run through a sampling protocol where several combinations of the separate transmitter and receiver elements are tested and the relative strength and/or quality of the return signals are assessed. The combination of one or more transmitter elements and one or more receiver elements providing the best signal is then utilized until another sampling protocol occurs. Such a sampling protocol may operate according to a predetermined schedule and/or may operate upon request, such as during part of an initial calibration process.

The transmitter array 472 (or the selected subset of transmitter elements within the array 472) are preferably operated in continuous wave (CW) mode, meaning the transmitter(s) are continuously transmitting the signal at the operating frequency. Although CW mode is preferred, other embodiments may be configured to operate in other modes, such as pulsed wave mode. The transmitted ultrasound signal radiates from the transmitter array 472 and propagates through tissues in the user's arm. Some of the ultrasound energy is reflected back to the receiver array 474. The reflected signal's frequency is shifted proportionally to the relative speed of objects in the transducer array's field of view (FOV), which includes blood flowing through the brachial artery past the transducer array. The receiver array 474 (or the selected subset of receiver elements within the array 474) receives the reflected ultrasound waves and operates to convert the ultrasound energy into an electronic voltage signal.

After passing through the receiving multiplexer 476, the voltage signal may be amplified using a suitable receiving amplifier 478, which is shown in this example as a low noise amplifier (LNA). The carrier portion of the signal generated by the oscillator 466 may then be removed from the amplified signal using a mixer 480. The mixer 480 receives the carrier signal (i.e., the 2 to 5 MHz signal) and the amplified signal passed from amplifier 478. Preferably, both the in-phase (I) and quadrature (Q) components of the mixed signal are generated at the mixer 480. This allows the system 400 to detect the difference between a Doppler frequency shift due to approaching particles and a shift due to receding particles.

The I and Q components from both the proximal and distal sensors may then be sampled by analog-to-digital converters (ADCs) 482 to digitize the Doppler signal received from the transducer arrays and enable further processing by the microprocessor 450 to determine PTT. The ADCs 482 are preferably operated at a sampling rate sufficient to maintain signal quality and avoid measurement degradation. A suitable sample rate, for example, may be about 10,000 samples per second (10 kSPS).

Figure 7:
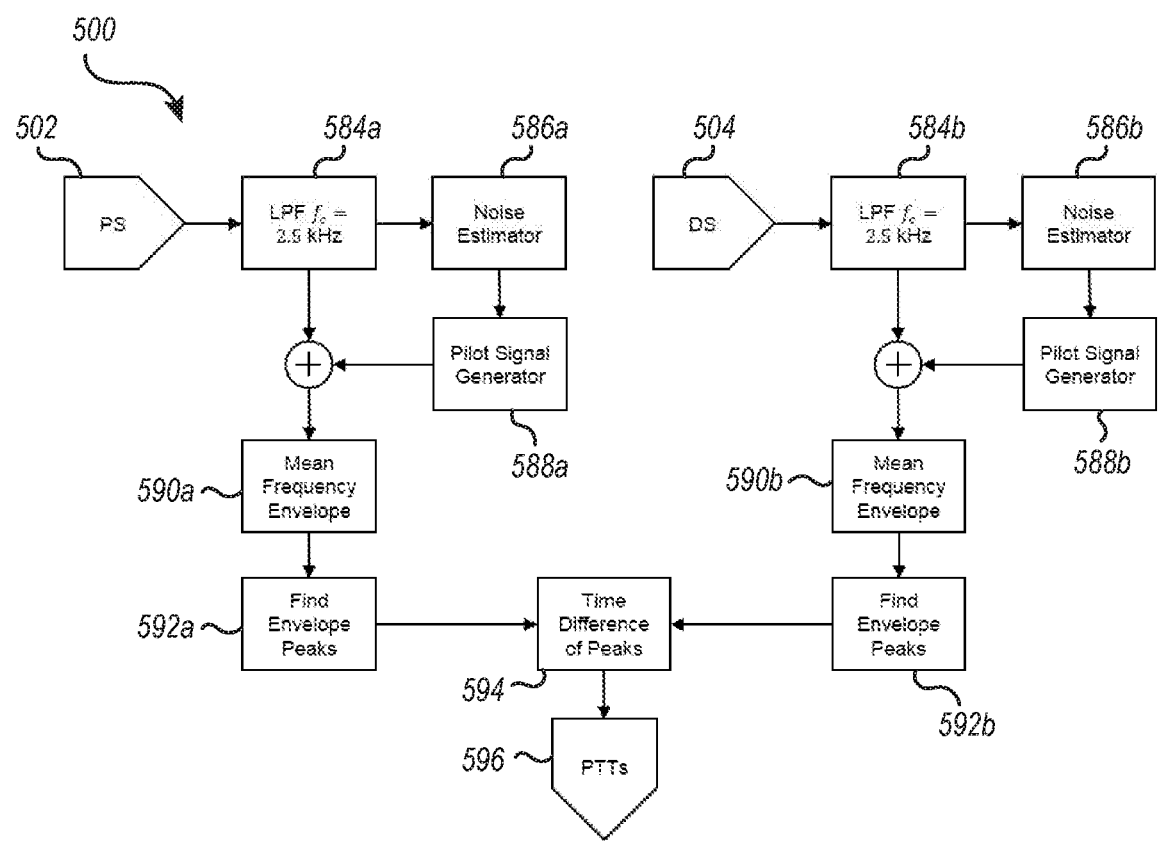
FIG. 7 schematically illustrates a system for generating a PTT measurement based on the ultrasound data provided by the ultrasound transducer arrays.

FIG. 7 illustrates a system 500 for generating a PTT measurement based on the ultrasound data provided by the ultrasound transducer arrays. The system 500 may be included, for example, within the microprocessor of the device such as microprocessor 350 and/or 450. The digitized signals from the proximal sensor 502 and distal sensor 504 may undergo similar operations. In FIG. 7, modules and/or operations related to the proximal sensor 502 include the subscript "a" and those related to the distal sensor 504 include the subscript "b". For simplicity, these modules and/or operations will be referred to in the singular without the qualifying subscript, and it will be understood that the same operation may be performed in the same manner on both sets of signals.

As shown, the digitized signals may be passed to a filter 584. In this example, the signal is filtered using a low-pass filter with a corner frequency of about 2.5 kHz, though other filtering parameters may be utilized to aid in increasing signal quality. A copy of the filtered signal is passed to a noise estimator 586. The noise estimator 586 operates by calculating the standard deviation of successive segments of the filtered signal, then selects the lowest calculated standard deviation as the noise level. Based on the determined noise level, a pilot signal generator 588 generates a pilot signal (having real and imaginary parts), and the pilot signal is added to another copy of the filtered signal.

The combined signals are then passed to a mean frequency estimator 590 which operates to generate a rough envelope of the mean frequency content of the signals. The mean frequency estimator may also operate to smooth the envelopes using one or more smoothing techniques known in the art to produce a cleaner signal. The envelopes are then passed to a peak finder module 592 which operates to determine the location of the peaks within the envelope. Each peak corresponds to the time when the speed of arterial blood flowing past the respective transducer array was at a maximum.

After identification of each peak, the separate proximal and distal envelopes are compared in a comparison module 594, which determines the time difference between corresponding proximal and distal peaks. Each such comparison generates a PTT estimate 596. The system 500 may group a selection of these PTT estimates over a predetermined time period and report an average (i.e., mean or median) as the measured PTT.

Terms such as "approximately," "about," and "substantially," as used herein represent an amount or condition close to the stated amount or condition that still performs a desired function or achieves a desired result. For example, the terms "approximately," "about," and "substantially" may refer to an amount or condition that deviates by less than 10%, or by less than 5%, or by less than 1%, or by less than 0.1%, or by less than 0.01% from a stated amount or condition.

Specific elements or components described in relation to any particular embodiment described herein may be substituted for or combined with elements described in relation to any other embodiment described herein. For example, any of the system or process embodiments shown in FIGS. 5 through 7 may make use of any of the monitoring device and/or transducer array embodiments shown in FIGS. 1A through 4D.

The invention claimed is:

1. A wearable monitoring device configured to measure a pulse transit time when worn by a user, the monitoring device comprising:
   a wearable fixture configured for securing the monitoring device to a limb of the user and including a first band and a second band which is disposed at a fixed distance from the first band along a longitudinal direction defined by the user's limb;
   a first transducer array attached to the first band of the wearable fixture, the first transducer array comprising a plurality of independent transducer elements for transmitting and receiving ultrasound energy;
   a second transducer array attached to the second band of the wearable fixture the second transducer array comprising a plurality of independent transducer elements for transmitting and receiving ultrasound energy;
   wherein the first band and the second band are connected via a slidable connection and are configured to rotate relative to one another along the slidable connection and around the longitudinal direction; and
   an electronics assembly operatively coupled to the first and second transducer arrays, the electronics assembly being configured to determine the pulse transit time between the first and second transducer arrays.

2. The monitoring device of claim 1, wherein the wearable fixture includes the first band coupled to the first transducer array and the second band coupled to the second transducer array.

3. The monitoring device of claim 2, wherein at least a portion of the electronics assembly is housed within a compartment that forms a portion of the first band or the second band.

4. The monitoring device of claim 1, wherein the wearable fixture includes a longitudinal section structurally separating the first and second transducer arrays.

5. The monitoring device of claim 1, wherein the wearable fixture includes a first housing in which the first transducer array is disposed and a second, separate housing in which the second transducer array is disposed.

6. The monitoring device of claim 1, wherein the fixed distance between the first and second bands ranges from about 1.5 to 6 inches.

7. The monitoring device of claim 1, wherein at least one of the first or second transducer arrays has a length ranging from about 0.5 to 4 inches.

8. The monitoring device of claim 1, wherein at least one of the first or second transducer arrays includes about 5 to 30 independent transducer elements.

9. The monitoring device of claim 1, wherein at least one of the first or second transducer arrays is configured to generate ultrasound waves with a frequency ranging from about 1.5 MHz to about 7 MHz.

10. The monitoring device of claim 1, wherein each transducer element of the first or second transducer array includes a transmitter and a corresponding receiver.

11. The monitoring device of claim 10, wherein the transmitters are aligned on one side of the first transducer array and the receivers are aligned on an opposite side of the first transducer array.

12. The monitoring device of claim 10, wherein the transmitters and receivers are positioned upon a block, and wherein the block is angled such that the transmitters and the receivers sit upon an angled surface.

13. The monitoring device of claim 1, wherein the first and second transducer arrays each include a layer of piezoelectric material.

14. The monitoring device of claim 1, wherein the first and second transducer arrays each include a layer of acoustically transparent material for acoustically coupling the first and second transducer arrays to the user's limb and for insulating said limb when the monitoring device is worn.

15. The monitoring device of claim 14, wherein the acoustically transparent material is a gel pad.

16. The monitoring device of claim 1, wherein the electronics assembly includes a communications module configured to communicatively couple the monitoring device to one or more external computer systems.

17. The monitoring device of claim 1, wherein the electronics assembly includes a motion sensor.

18. The monitoring device of claim 1, wherein the electronics assembly comprises a microprocessor configured to, for at least one of the first or second transducer array, determine a particular subset of transmitter elements within the at least one of the first or second transducer array through which ultrasound energy is transmitted where the selected subset of transmitter elements are the one or more transmitter elements determined as being closest to an artery.

19. The monitoring device of claim 1, wherein the electronics assembly comprises a microprocessor configured to, for at least one of the first or second transducer array, determine a particular subset of receiver elements within the at least one of the first or second transducer array through which a reflected ultrasound signal is obtained where the selected subset of receiver elements are the one or more receiver elements determined as being closest to an artery.

20. A method of determining pulse transit time across an arterial distance, the method comprising:
- providing a wearable monitoring device as in claim 1;
- positioning the wearable monitoring device on the user in an operational position; and
- operating the wearable monitoring device to obtain one or more pulse transit time measurements.

21. The method of claim 20, wherein the wearable monitoring device is positioned on the user's upper arm.

22. The method of claim 21, wherein the wearable monitoring device is positioned such that the first and second transducer arrays are on an inner arm adjacent the user's brachial artery.

23. A wearable monitoring device configured to measure a pulse transit time when worn by a user, the monitoring device comprising:
- a wearable fixture configured for securing the monitoring device to a limb of the user;
- a first transducer array attached to a first band of the wearable fixture, the first transducer array comprising a plurality of independent transducer elements for transmitting and receiving ultrasound energy;
- a second transducer array attached to a second band of the wearable fixture, the second transducer array comprising a plurality of independent transducer elements for transmitting and receiving ultrasound energy, wherein the second band is disposed at a fixed distance from the first band along a longitudinal direction defined by the user's limb;
- a slidable connection disposed between the first band and the second band and configured to connect the first band and the second band, wherein the first band and the second band rotate relative to one another along the slidable connection and around the longitudinal direction;
- an electronics assembly operatively coupled to the first and second transducer arrays, the electronics assembly being configured to determine the pulse transit time between the first and second transducer arrays; and
- a microprocessor configured to, for at least one of the first or second transducer array, determine a particular subset of transducers through which ultrasound energy is transmitted and a reflected ultrasound signal is obtained, wherein the selected subset of transducers are the one or more transducers determined as being closest to a target artery.

* * * * *